(12) United States Patent
Fukuyo et al.

(10) Patent No.: US 12,077,615 B2
(45) Date of Patent: Sep. 3, 2024

(54) METHOD OF PRODUCING POLYMERIZABLE COMPOSITION AND POLYMERIZABLE COMPOSITION

(71) Applicant: GC Corporation, Shizuoka (JP)

(72) Inventors: Yuri Fukuyo, Tokyo (JP); Takayuki Ueno, Tokyo (JP); Makoto Takahashi, Tokyo (JP); Hiroki Kato, Tokyo (JP); Yuki Kasai, Tokyo (JP)

(73) Assignee: GC Corporation, Shizuoka (JP)

( * ) Notice: Subject to any disclaimer, the term of this patent is extended or adjusted under 35 U.S.C. 154(b) by 0 days.

(21) Appl. No.: 17/443,357

(22) Filed: Jul. 26, 2021

(65) Prior Publication Data
US 2022/0033533 A1    Feb. 3, 2022

(30) Foreign Application Priority Data
Jul. 28, 2020   (JP) .................................. 2020-127566

(51) Int. Cl.
| | | |
|---|---|---|
| *C08F 2/08* | (2006.01) | |
| *C08F 20/12* | (2006.01) | |
| *C08L 33/10* | (2006.01) | |

(52) U.S. Cl.
CPC ................ *C08F 2/08* (2013.01); *C08F 20/12* (2013.01); *C08L 33/10* (2013.01); *C08L 2201/56* (2013.01)

(58) Field of Classification Search
CPC ....................................................... C08F 2/08
See application file for complete search history.

(56) References Cited

U.S. PATENT DOCUMENTS

| | | | |
|---|---|---|---|
| 5,408,022 A | 4/1995 | Imazato et al. | |
| 2003/0064102 A1* | 4/2003 | Nakatsuka | A61P 31/02 424/486 |

FOREIGN PATENT DOCUMENTS

| | | |
|---|---|---|
| CN | 106749878 | 5/2019 |
| EP | 1548751 | 6/2005 |
| JP | H02-311852 | 12/1990 |
| JP | H06-009725 | 1/1994 |
| JP | 2016-532162 | 10/2016 |
| WO | 2010/081104 | 7/2010 |
| WO | 2013/155608 | 10/2013 |

OTHER PUBLICATIONS

Kim et al (Studies on the preparation and dental properties of antibacterial polymeric dental restorative composites containing alkylated ammonium chloride derivatives, J of Polymer Research vol. 8, No. 1, 49-57, Mar. 2001) (Year: 2001).*

* cited by examiner

*Primary Examiner* — Wenwen Cai
(74) *Attorney, Agent, or Firm* — IPUSA, PLLC

(57) ABSTRACT

There is provided a method of producing a polymerizable composition that includes a first polymerizable monomer; and a second polymerizable monomer, a polymer of the second polymerizable monomer, or both, the second polymerizable monomer, the polymer of the second polymerizable monomer, or the both being dispersed in the first polymerizable monomer, the method of producing a polymerizable composition includes dissolving the first polymerizable monomer; the second polymerizable monomer, the polymer of the second polymerizable monomer, or the both in a solvent to obtain a solution in a first step; and evaporating the solvent from the solution in a second step, wherein the first polymerizable monomer is a liquid, and wherein the second polymerizable monomer is a solid.

4 Claims, 2 Drawing Sheets

HL D4.4 x300 300 μm

HL D4.4 x1.0k 100 μm

METHOD OF PRODUCING POLYMERIZABLE COMPOSITION AND POLYMERIZABLE COMPOSITION

CROSS-REFERENCE TO RELATED APPLICATION

The present application is based on and claims priority to Japanese patent application No. 2020-127566 filed on Jul. 28, 2020, with the Japanese Patent Office, the entire contents of which are hereby incorporated by reference.

BACKGROUND OF THE INVENTION

1. Field of the Invention

The disclosures herein relate to a method of producing a polymerizable composition and a polymerizable composition.

2. Description of the Related Art

In the dental field, there is a need to impart antibacterial properties to a cured product of a dental polymerizable composition such as a dental composite resin and the like.

Patent Document 1 discloses a polymerizable composition including an ethylenically unsaturated monomer, at least one monomer selected from a monofunctional compound to a trifunctional compound having specific antibacterial properties, and a polymerization initiator.

Patent Document 1: Japanese Patent Application Laid-Open No. H6-9725

SUMMARY OF THE INVENTION

However, a problem with the disclosed composition that an appearance of the cured product of the dental polymerizable composition is deteriorated.

One aspect of the invention is to provide a method of producing a polymerizable composition capable of improving the appearance of a cured product of a polymerizable composition.

One aspect of the invention is a method of producing a polymerizable composition that includes a first polymerizable monomer; and a second polymerizable monomer, a polymer of the second polymerizable monomer, or both, the second polymerizable monomer, the polymer of the second polymerizable monomer, or the both being dispersed in the first polymerizable monomer, the method of producing a polymerizable composition including: dissolving the first polymerizable monomer; the second polymerizable monomer, the polymer of the second polymerizable monomer, or the both in a solvent to obtain a solution in a first step; and evaporating the solvent from the solution in a second step, wherein the first polymerizable monomer is a liquid, and wherein the second polymerizable monomer is a solid.

According to one aspect of the invention, a method of producing a polymerizable composition capable of improving the appearance of a cured product of a polymerizable composition can be provided.

DESCRIPTION OF THE PREFERRED EMBODIMENTS

Figure 1A:
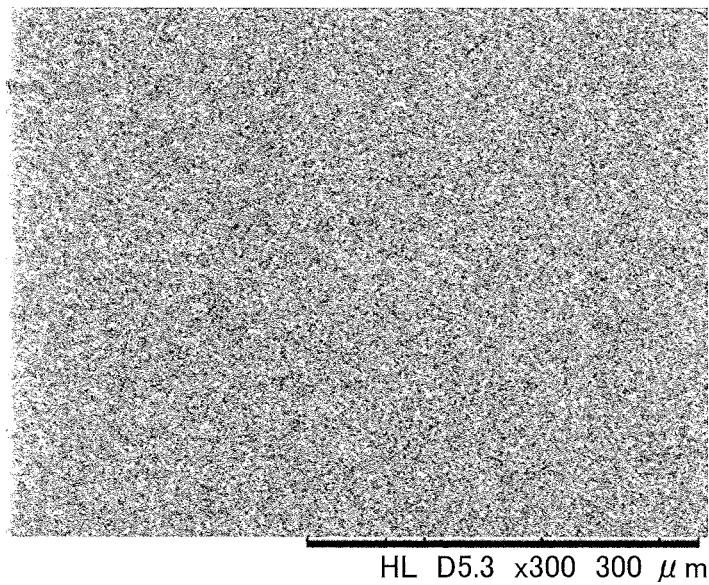
FIG. 1A indicates a SEM image of a surface of a specimen in Examples 1 to 3.

Next, embodiments for carrying out the present invention will be described.

<Method of Producing Polymerizable Composition>

A method of producing a polymerizable composition according to the present embodiment is a method of producing a polymerizable composition in which a second polymerizable monomer, a polymer of a second polymerizable monomer, or both are dispersed in a first polymerizable monomer.

Here, the polymer of the second polymerizable monomer may be a homopolymer of the second polymerizable monomer or a copolymer of the second polymerizable monomer and a polymerizable monomer other than the second polymerizable monomer.

The polymerizable monomer other than the second polymerizable monomer may be a first polymerizable monomer or a polymerizable monomer other than the first polymerizable monomer.

A method of producing a polymerizable composition of the present embodiment includes a first step and a second step. The first step includes obtaining a solution in which the first polymerizable monomer, the second polymerizable monomer and/or the polymer of the second polymerizable monomer are dissolved in a solvent. The second step includes evaporating the solvent from the solution.

Here, the first polymerizable monomer is a liquid and the second polymerizable monomer is a solid. For example, the first polymerizable monomer is a liquid at room temperature and atmospheric pressure, and the second polymerizable monomer is a solid at room temperature and atmospheric pressure.

In this case, if the first polymerizable monomer is directly mixed with the second polymerizable monomer and/or the polymer of the second polymerizable monomer, it is difficult to control the particle size of the second polymerizable monomer and/or the polymer of the second polymerizable monomer, and the appearance of the cured product of the polymerizable composition would be deteriorated.

Meanwhile, when the solvent is evaporated from a solution in which the first polymerizable monomer, the second polymerizable monomer and/or the polymer of the second polymerizable monomer are dissolved in a solvent, the particle size of the second polymerizable monomer and/or the polymer of the second polymerizable monomer can be controlled. As a result, the appearance of the cured product of the polymerizable composition can be improved while providing performance from the second polymerizable monomer to the cured product. For example, if the second polymerizable monomer has a functional group that exhibits antibacterial properties, the second polymerizable monomer can impart antibacterial properties to the cured product of the polymerizable composition.

The mass ratio of the first polymerizable monomer to the second polymerizable monomer and/or the polymer of the second polymerizable monomer is preferably in the range of 0.01 to 1000, and more preferably in the range of 0.04 to 100. When the mass ratio of the first polymerizable monomer to the second polymerizable monomer and/or the polymer of the second polymerizable monomer is 0.01 or more, the appearance of the cured product of the polymerizable composition is improved. When the mass ratio of the first polymerizable monomer to the second polymerizable monomer and/or the polymer of the second polymerizable monomer is 1000 or less, the properties derived from the second polymerizable monomer of the cured product of the polymerizable composition are improved.

In the present embodiment, a photopolymerization initiator, a tertiary amine, a polymerization inhibitor, or the like is preferably added to obtain the solution.

In addition, a filler or the like is preferably added after the solvent is evaporated from the solution.

The first step preferably includes a step of dissolving at least a portion of the first polymerizable monomer and the second polymerizable monomer in a solvent to obtain a first solution. Accordingly, the second polymerizable monomer in the polymerizable composition is well dispersed, and as a result, the appearance of the cured product of the polymerizable composition is improved.

In this case, a photopolymerization initiator, a tertiary amine, a polymerization inhibitor, or the like is preferably added to the remainder of the first polymerizable monomer.

When a portion of the first polymerizable monomer is used in obtaining the first solution, a dispersion liquid and the remainder of the first polymerizable monomer are mixed after obtaining the dispersion liquid.

The mass ratio of the second polymerizable monomer to at least a portion of the first polymerizable monomer is preferably in the range of 0.001 to 100, and more preferably in the range of 0.01 to 50. When the mass ratio of the second polymerizable monomer to at least a portion of the first polymerizable monomer is 0.001 or more and 100 or less, the second polymerizable monomer in the polymerizable composition is well dispersed.

A content of the solvent in the first solution is preferably in the range of 50 to 99.9% by mass. When the content of the solvent in the first solution is 50% by mass or more, the dissolution stability of the first solution is improved, and when the content is 99.9% by mass or less, the solvent is easily evaporated from the first solution.

The first step preferably includes a step of dissolving a portion of the first polymerizable monomer and the second polymerizable monomer in a solvent to obtain the first solution, a step of heating the first solution to obtain a second solution by copolymerizing a portion of the first polymerizable monomer with the second polymerizable monomer, and a step of mixing the second solution with at least a portion of the remainder of the first polymerizable monomer to obtain a third solution. Accordingly, a copolymer of the first polymerizable monomer and the second polymerizable monomer as a polymer of the second polymerizable monomer is obtained. Therefore, the polymer of the second polymerizable monomer in the polymerizable composition is well dispersed, and as a result, the appearance of the cured product of the polymerizable composition is improved.

In this case, a thermal polymerization initiator is preferably added to the solvent. A photopolymerization initiator, a tertiary amine, a polymerization inhibitor, or the like is preferably added to the remainder of the first polymerizable monomer.

Here, when a portion of the remainder of the first polymerizable monomer is used to obtain the third solution, the dispersion liquid and the remainder of the first polymerizable monomer are mixed after obtaining the dispersion liquid.

The mass ratio of the second polymerizable monomer to at least a portion of the first polymerizable monomer is preferably in the range of 0.001 to 100, and more preferably in the range of 0.01 to 50. When the mass ratio of the second polymerizable monomer to at least a portion of the first polymerizable monomer is 0.001 or more and 100 or less, the polymer of the second polymerizable monomer in the polymerizable composition is well dispersed.

The content of the solvent in the first solution is preferably in the range of 50 to 99.9% by mass. When the content of the solvent in the first solution is 50% by mass or more, the dissolution stability of the first solution is improved, and when the content is 99.9% by mass or less, the solvent is easily evaporated from the first solution.

<First Polymerizable Monomer>

The first polymerizable monomer is preferably a (meth)acrylate and is further preferably a multifunctional (meth)acrylate having two or more (meth)acryloyloxy groups.

Examples of the first polymerizable monomer include ethoxylated bisphenol A dimethacrylate, neopentylglycol dimethacrylate, urethane dimethacrylate, glycerin dimethacrylate, triethylene glycol dimethacrylate, and the like. Two or more kinds of monomers may be used in combination.

<Second Polymerizable Monomer>

The second polymerizable monomer is insoluble in the first polymerizable monomer.

The second polymerizable monomer is preferably a (meth)acrylate and is further preferably a monofunctional (meth)acrylate having one (meth)acryloyloxy group.

The second polymerizable monomer preferably has groups exhibiting antibacterial properties.

Examples of groups exhibiting antibacterial properties include a quaternary ammonium base and the like.

Examples of the second polymerizable monomers having groups exhibiting antibacterial properties include monofunctional polymerizable monomers such as 2-(methacryloyloxy) ethyltrimethylammonium chloride, dimethylaminopropylacrylamide methyl chloride quaternary salt, dimethylaminoethyl acrylate methyl chloride quaternary salt, dimethylaminoethyl acrylate benzyl chloride quaternary salt, (3-acrylamidepropyl) trimethylammonium chloride, (2-(acryloyloxy)ethyl) trimethylammonium chloride, and the like; a multifunctional polymerizable monomer of the chemical compounds represented by the following chemical formula and the like. Two or more kinds of polymerizable monomers may be used in combination.

[Chemical Formula 1]

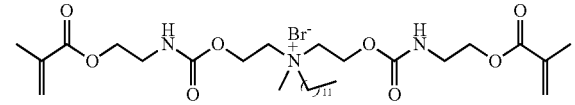

Examples of the second polymerizable monomer that do not have groups exhibiting antibacterial properties include phenoxyethylene glycol methacrylate, dimethylaminoethyl methacrylate, and the like.

The second polymerizable monomer may be used alone or in combination with two or more kinds.

<Solvent>

The solvent is not particularly limited as long as the first polymerizable monomer and the second polymerizable monomer are able to be dissolved in the solvent. For example, the solvent is an organic solvent such as ethanol, acetone, hexane, chloroform, and the like. Two or more kinds of solvents may be used in combination.

<Photopolymerization Initiator>

Examples of photopolymerization initiators include camphorquinone, phenylbis (2,4,6-trimethylbenzoyl) phosphine oxide, 2,4,6-trimethylbenzoyl diphenylphosphine oxide, benzyl ketal, diacetyl ketal, benzyl dimethyl ketal, benzyl diethyl ketal, benzylbis (2-methoxyethyl) ketal, 4,4'-dimethyl (benzyldimethyl ketal), anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, benzoin isopropyl ether, benzoin isobutyl ether, benzophenone, bis (4-dimethylaminophenyl) ketone, 4,4'-bis (diethylamino)benzophenone, and the like. Two or more kinds may be used in combination.

<Tertiary Amine>

The tertiary amine may be either a tertiary aliphatic amine or a tertiary aromatic amine, but is preferably a tertiary aromatic amine and particularly preferably alkyl p-dialkylaminobenzoate.

Examples of the tertiary aliphatic amines include N,N-dimethylaminoethylmethacrylate, triethanolamine, and the like.

Examples of alkyl p-dialkylaminobenzoates include methyl p-dimethylaminobenzoate, ethyl p-dimethylaminobenzoate, propyl p-dimethylaminobenzoate, amyl p-dimethylaminobenzoate, isoamyl p-dimethylaminobenzoate, ethyl p-diethylaminobenzoate, propyl p-diethylaminobenzoate, and the like.

Examples of tertiary aromatic amines other than alkyl p-dialkylaminobenzoate include 7-dimethylamino-4-methylcoumarin, N,N-dimethylaniline, N,N-dibenzylaniline, N,N-dimethyl-p-toluidine, N,N-diethyl-p-toluidine, N,N-bis (2-hydroxyethyl)-p-toluidine, N,N,2,4,6-pentamethylaniline, N,N,2,4-tetramethylaniline, N,N-diethyl-2,4,6-trimethylaniline, and the like.

The tertiary amine may be used alone or in combination with two or more kinds.

<Polymerization Inhibitor>

Examples of the polymerization inhibitors include dibutyl hydroxytoluene (2,6-di-tert-butyl-p-cresol), 6-tert-butyl-2,4-xylenol, and the like. Two or more kinds may be used in combination.

<Filler>

Examples of the fillers include anhydrous silicic acid powder, fumed silica, alumina powder, glass powder (for example, barium glass powder, fluoroaluminosilicate glass powder), and the like. Two or more kinds may be used in combination.

The filler may be treated with a surface treatment agent such as a silane coupling agent.

<Thermal Polymerization Initiator>

Examples of thermal initiators include 2,2'-azobis (2-methylpropionate) dimethyl, 2,2'-azobis (isobutyronitrile), 2,2'-azobis (2,4-dimethylvaleronitrile), 2,2'-azobis (2-methylbutyronitrile), 1,1'-azobis (cyclohexanecarbonitrile), 2,2'-azobis (4-methoxy-2,4-dimethylvaleronitrile), 4,4'-azobis (4-cyanovaleric acid), 2,2'-azobis [2-methyl-N-(2-hydroxyethyl) propionamide], 2,2'-azobis [N-(2-carboxyethyl)-2-methylpropionamidine]n hydrate, 2,2'-azobis (2-methylpropionamidine) dihydrochloride, 2,2'-azobis [2-(2-imidazoline-2-yl) propane], 2,2'-azobis [2-(2-imidazoline-2-yl) propane]dihydrochloride, and the like. Two or more kinds may be used in combination.

<Polymerizable Composition>

With respect to a polymerizable composition of the present embodiment, a second polymerizable monomer and/or a polymer of a second polymerizable monomer is dispersed in a first polymerizable monomer. Here, the first polymerizable monomer is a liquid and the second polymerizable monomer is a solid.

The particle size of the second polymerizable monomer and/or the polymer of the second polymerizable monomer in the polymerizable composition of the present embodiment is preferably in the range of 0.01 to 500 μm and further preferably in the range of 0.1 to 100 μm. When the particle size of the second polymerizable monomer and/or the polymer of the second polymerizable monomer in the polymerizable composition of the present embodiment is 0.01 μm or more, the performance derived from the second polymerizable monomer of the cured product of the polymerizable composition of the present embodiment is improved. When the particle size is 500 μm or less, the appearance of the cured product of the polymerizable composition of the present embodiment is improved.

The content of the first polymerizable monomer in the polymerizable composition of the present embodiment is preferably in the range of 1 to 99% by mass and further preferably in the range of 2 to 50% by mass. When the content of the first polymerizable monomer in the polymerizable composition of the present embodiment is 18 by mass or more, the appearance of the cured product of the polymerizable composition of the present embodiment is improved. When the content is 99% by mass or less, the performance derived from the second polymerizable monomer of the cured product of the polymerizable composition of the present embodiment is improved.

The content of the second polymerizable monomer in the polymerizable composition of the present embodiment is preferably in the range of 0.01 to 99% by mass and further preferably in the range of 0.1 to 30% by mass. When the content of the second polymerizable monomer in the polymerizable composition of the present embodiment is 0.01% by mass or more, the performance derived from the second polymerizable monomer of the cured product of the polymerizable composition of the present embodiment is improved. When the content is 99% by mass or less, the appearance of the cured product of the polymerizable composition of the present embodiment is improved.

The content of the solvent in the polymerizable composition of the present embodiment is preferably 0.5% by mass or less and further preferably 0.1% by mass or less. When the content of the solvent in the polymerizable composition of the present embodiment is 0.5% by mass or less, the strength of the cured product of the polymerizable composition of the present embodiment is improved.

The polymerizable composition of the present embodiment is preferably a dental polymerizable composition.

Examples of dental polymerizable compositions include dental composite resins, dental cement, denture bed resins, denture universal resins, and the like. Of these, dental composite resins are preferably used.

Also, the cured product of the dental polymerizable composition can be applied to, for example, a dental resin block or the like.

Example

Hereinafter, examples of the present invention will be described, but the present invention is not limited to the examples.

<Preparation of Liquid Composition>

3.5 g of ethoxylated bisphenol A dimethacrylate (hereinafter referred to as BisMEPP) and 7.2 g of neopentylglycol dimethacrylate (hereinafter referred to as NPG) were mixed to prepare a first polymerizable monomer. 0.01 g of (+)-camphorquinone, and 0.03 g of ethyl p-dimethylaminobenzoate were then mixed with the first polymerizable monomer to obtain a liquid composition (1).

3.5 g of BisMEPP and 3 g of NPG were mixed to prepare a first polymerizable monomer. 0.01 g of (+)-camphorquinone and 0.03 g of ethyl p-dimethylaminobenzoate were then mixed with the first polymerizable monomer to obtain a liquid composition (2).

Example 1-1

A first polymerizable monomer including 3.3 g of BisMEPP and 6.5 g of NPG, a second polymerizable monomer including 2.5 g of 2-(methacryloyloxy)ethyltrimethylammonium chloride (hereinafter referred to as MTMAC), 0.01 g of (±)-camphorquinone, and 0.04 g of ethyl p-dimethylaminobenzoate were dissolved in 100 mL of ethanol to obtain a first solution.

The ethanol was evaporated from the first solution at 30 to 40° C. under reduced pressure using an evaporator to obtain a dispersion liquid in which the second polymerizable monomer was dispersed in the first polymerizable monomer.

0.9 g of the dispersion liquid, 3.3 g of fluoroaluminosilicate glass powder, which had been surface-treated with 3-glycidyloxytrimethoxysilane having 0.4 μm in median diameter, and 1.8 g of the liquid composition (1) were mixed and kneaded with an automatic mortar to obtain a dental composite resin.

Example 1-2

4.7 g of BisMEPP, 9.5 g of NPG, 2.5 g of MTMAC, 0.01 g of (+)-camphorquinone, and 0.04 g of ethyl p-dimethylaminobenzoate were dissolved in 100 mL of ethanol to obtain a first solution.

The ethanol was evaporated from the first solution at 30 to 40° C. under reduced pressure using an evaporator to obtain a dispersion liquid in which the second polymerizable monomer was dispersed in the first polymerizable monomer.

1.2 g of the dispersion liquid, 3.3 g of fluoroaluminosilicate glass powder, which had been surface-treated with 3-glycidyloxytrimethoxysilane with a median diameter of 0.4 μm, and 1.5 g of the liquid composition (1) were mixed and kneaded with an automatic mortar to obtain a dental composite resin.

Example 1-3

12.0 g of BisMEPP, 24.5 g of NPG, 2.5 g of MTMAC, 0.01 g of (+)-camphorquinone, and 0.04 g of ethyl p-dimethylaminobenzoate were dissolved in 100 mL of ethanol to obtain a first solution.

The ethanol was evaporated from the first solution at 30 to 40° C. under reduced pressure using an evaporator to obtain a dispersion liquid in which the second polymerizable monomer was dispersed in the first polymerizable monomer.

2.7 g of the dispersion liquid and 3.3 g of fluoroaluminosilicate glass powder, which had been surface-treated with 3-glycidyloxytrimethoxysilane with a median diameter of 0.4 μm were mixed with an automatic mortar to obtain a dental composite resin.

Example 1-4

A dental composite resin was obtained in the same manner as Example 1-1 except that 3-(acrylamide propyl) trimethylammonium chloride (hereinafter referred to as AATMAC) was used as a second polymerizable monomer.

Example 1-5

A dental composite resin was obtained in the same manner as Example 1-1 except that (2-(acryloyloxy)ethyl) trimethylammonium chloride (hereinafter referred to as ATMAC) was used as a second polymerizable monomer.

Example 1-6

1.5 g of BisMEPP, 3.0 g of NPG, 0.9 g of MTMAC, 0.02 g of (+)-camphorquinone, and 0.04 g of ethyl p-dimethylaminobenzoate were dissolved in 100 mL of ethanol to obtain a first solution.

The ethanol was evaporated from the first solution at 30 to 40° C. under reduced pressure using an evaporator to obtain a dispersion liquid in which the second polymerizable monomer was dispersed in the first polymerizable monomer.

0.9 g of the dispersion liquid, 3.3 g of fluoroaluminosilicate glass powder, which had been surface-treated with 3-glycidyloxytrimethoxysilane with a median diameter of 0.4 μm, and 1.8 g of the liquid composition (1) were mixed and kneaded with an automatic mortar to obtain a dental composite resin.

Example 2-1

20 g of NPG as a first polymerizable monomer and 20 g of MTMAC as a second polymerizable monomer were dissolved in 1 L of ethanol to obtain a first solution. The first solution was then stirred at 70° C. for 15 hours, then cooled to room temperature with flowing water to obtain a second solution. 90 g of the second solution and 5.5 g of the liquid composition (2) were then stirred to obtain a third solution.

The ethanol was evaporated from the third solution at 30 to 40° C. under reduced pressure using an evaporator to obtain a dispersion liquid in which a polymer of the second polymerizable monomer was dispersed in the first polymerizable monomer.

0.9 g of the dispersion liquid, 3.3 g of fluoroaluminosilicate glass powder, which had been surface-treated with 3-glycidyloxytrimethoxysilane with a median diameter of 0.4 μm, and 1.8 g of the liquid composition (1) were mixed and kneaded with an automatic mortar to obtain a dental composite resin.

Example 2-2

20 g of NPG, 20 g of MTMAC, and 0.05 g of 2,2'-azobis (2-methylpropionic acid) dimethyl were dissolved in 1 L of ethanol to obtain a first solution. The first solution was then stirred at 55° C. for 15 hours, copolymerized with NPG and MTMAC, and cooled to room temperature with flowing water to obtain a second solution. 90 g of the second solution and 5.5 g of the liquid composition (2) were then stirred to obtain a third solution.

The ethanol was evaporated from the third solution at 30 to 40° C. under reduced pressure using an evaporator to obtain a dispersion liquid in which a polymer of the second polymerizable monomer was dispersed in the first polymerizable monomer.

0.9 g of the dispersion liquid, 3.3 g of fluoroaluminosilicate glass powder, which had been surface-treated with 3-glycidyloxytrimethoxysilane with a median diameter of 0.4 μm, and 1.8 g of the liquid composition (1) were mixed and kneaded with an automatic mortar to obtain a dental composite resin.

Comparative Example 1

0.3 g of MTMAC, 3.3 g of fluoroaluminosilicate glass powder, which had been surface-treated with 3-glycidyloxytrimethoxysilane with a median diameter of 0.4 μm in median diameter, and 2.4 g of the liquid composition (1) were mixed and kneaded with an automatic mortar to obtain a dental composite resin.

Comparative Example 2

2 g of MTMAC and 10 mL of liquid nitrogen were charged into a cryogenic sample crusher and then crushed for 5 minutes. However, as the crushed MTMAC started to absorb moisture immediately after removal from the cryogenic sample crusher and deliquesced, a dental composite resin was not obtained because the crushed MTMAC was not obtained as powder.

Next, the appearance and antibacterial effect of the cured products of the dental composite resins were evaluated.

<Preparation of Test Piece>

A dental composite resin was poured into a silicone mold that was 1 cm in diameter and 5 mm in thickness, and then cured using a dental light irradiator. The surface of the resulting cured product was polished with water by using a water-resistant polishing paper #4000 to obtain a test piece.

<Appearance of Cured Product>

The surface of the test piece was visually observed and the appearance of the cured product was evaluated.

The criteria for determining the appearance of the cured product were as follows.

Excellent: The surface of the test piece was uniform.

Poor: The surface of the test piece was uneven.

<Antibacterial Effect of Cured Product>

The surface of the test piece was observed with SEM to evaluate the antibacterial effect of the cured product.

Figure 1B:
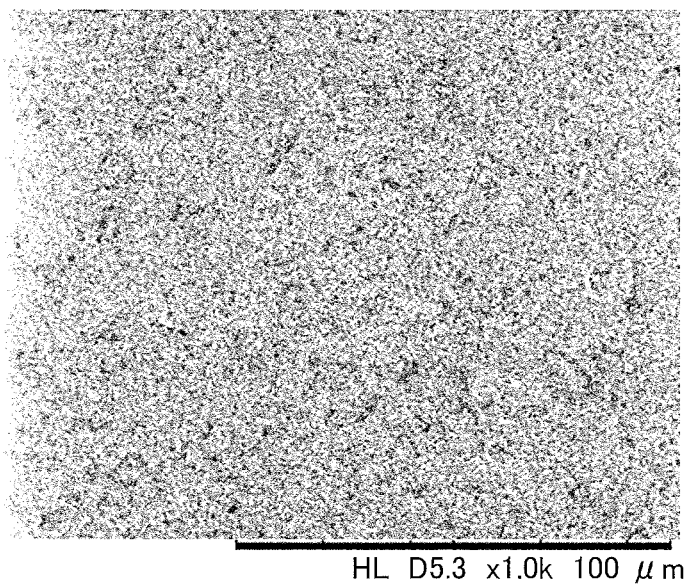
FIG. 1B indicates a SEM image of a surface of a specimen in Examples 1 to 3.
Figure 2A:
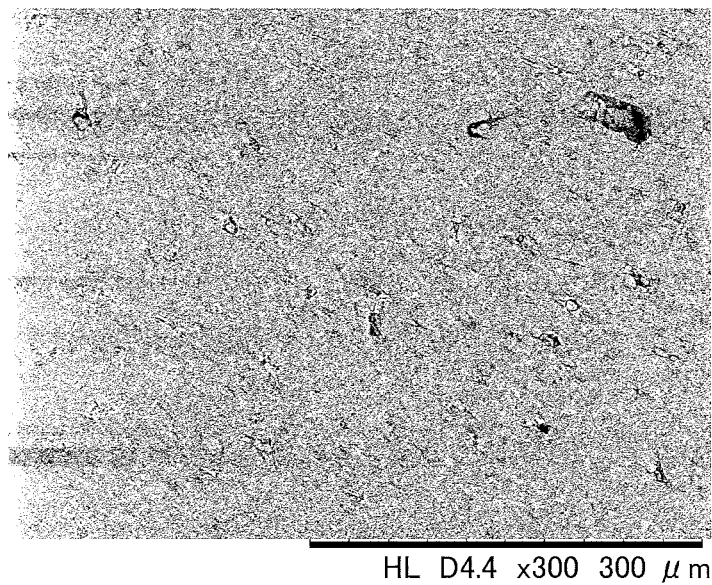
FIG. 2A indicates a SEM image of a surface of a specimen in Comparative Example 1.
Figure 2B:
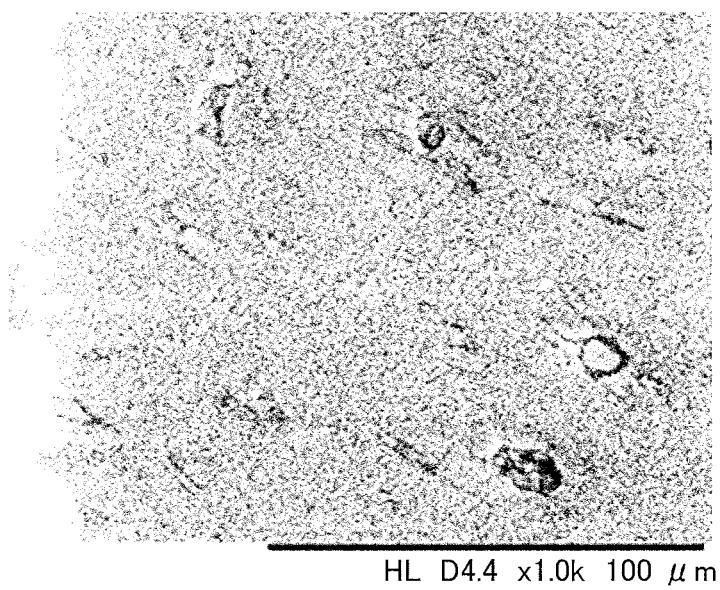
FIG. 2B indicates a SEM image of a surface of a specimen in Comparative Example 1.

FIGS. 1 and 2 illustrate SEM images of the surface of the test pieces in Example 1-3 and Comparative Example 1. FIGS. 1A and 2A are SEM images of 300 times magnification, and FIGS. 1B and 2B are SEM images of 1000 times magnification.

The criteria for determining the antibacterial effect of the cured product were as follows.

Excellent: Presence of particles of polymer of MTMAC on the surface of the test piece was observed.

Poor: Absence of particles of polymer of MTMAC on the surface of the test piece was observed.

In general, antibacterial effect of a cured product is excellent when particles of polymer having groups exhibiting antibacterial properties present on the surface of the cured product.

Table 1 indicates the evaluation results of the appearance and antibacterial effect of the cured products of the dental composite resins.

TABLE 1

| | Example 1 | | | | | | Example 2 | | Comparative |
|---|---|---|---|---|---|---|---|---|---|
| | 1 | 2 | 3 | 4 | 5 | 6 | 1 | 2 | Example 1 |
| First polymerizable monomer | BisMEPP NPG | BisMEPP NPG | BisMEPP NPG | BisMEPP NPG | BisMEPP NPG | BisMEPP NPG | BisMEPP NPG | BisMEPP NPG | BisMEPP NPG |
| Second polymerizable monomer | MTMAC | MTMAC | MTMAC | AATMAC | ATMAC | MTMAC | MTMAC | MTMAC | MTMAC |
| Solvent | Ethanol | Ethanol | Ethanol | Ethanol | Ethanol | Ethanol | Ethanol | Ethanol | — |
| Apperance of cured product | Excellent | Excellent | Excellent | Excellent | Excellent | Excellent | Excellent | Excellent | Poor |
| Antibacterial effect | Excellent | Excellent | Excellent | Excellent | Excellent | Excellent | Excellent | Excellent | Excellent |

Table 1 indicates that the dental composite resins of Examples 1-1 to 1-6 and Examples 2-1 to 2-2 were excellent in the appearance and antibacterial effect of the cured products.

In contrast, the appearance of the cured product in Comparative Example 1 was poor because the dental composite resin in Comparative Example 1 was produced without using the solvent.

What is claimed is:

1. A method of producing a polymerizable composition, the method comprising:
    dissolving (i) a portion of a first polymerizable monomer and (ii) a second polymerizable monomer in a solvent to obtain a first solution;
    heating the first solution to copolymerize the portion of the first polymerizable monomer and the second polymerizable monomer to obtain a second solution;
    mixing the second solution with at least a portion of a remainder of the first polymerizable monomer to obtain a third solution;
    evaporating the solvent from the third solution to obtain a dispersion liquid in which the copolymer of the second polymerizable monomer is dispersed in the first polymerizable monomer; and
    after the evaporating step, mixing and kneading the dispersion liquid and a filler,
    wherein the first polymerizable monomer is a liquid at room temperature and atmospheric pressure, and
    wherein the second polymerizable monomer is a solid at room temperature and atmospheric pressure.

2. The method of producing the polymerizable composition according to claim 1, wherein one or both of the first polymerizable monomer and the second polymerizable monomer is a (meth)acrylate.

3. The method of producing the polymerizable composition according to claim 1, wherein the second polymerizable monomer includes a functional group that exhibits an antibacterial property.

4. A method of producing a polymerizable composition that includes a first polymerizable monomer and a copolymer of a second polymerizable monomer, the copolymer of the second polymerizable monomer being dispersed in the first polymerizable monomer, the method of producing the polymerizable composition comprising:
- dissolving (i) a portion of a first polymerizable monomer and (ii) a second polymerizable monomer in a solvent to obtain a first solution;
- heating the first solution to copolymerize the portion of the first polymerizable monomer and the second polymerizable monomer to obtain a second solution;
- mixing the second solution with at least a portion of a remainder of the first polymerizable monomer to obtain a third solution; and
- evaporating the solvent from the third solution,
- wherein the first polymerizable monomer is a liquid, and
- wherein the second polymerizable monomer is a solid.

* * * * *